United States Patent
Erickson et al.

(10) Patent No.: US 7,047,084 B2
(45) Date of Patent: May 16, 2006

(54) APPARATUS FOR DIRECTIONALLY STIMULATING NERVE TISSUE

(75) Inventors: John H. Erickson, Plano, TX (US); Terry D. Daglow, Allen, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 588 days.

(21) Appl. No.: 10/300,434

(22) Filed: Nov. 20, 2002

(65) Prior Publication Data

US 2004/0098074 A1    May 20, 2004

(51) Int. Cl.
*A61N 1/04* (2006.01)

(52) U.S. Cl. .................................. 607/116; 600/373
(58) Field of Classification Search ............. 607/117
See application file for complete search history.

(56) References Cited

U.S. PATENT DOCUMENTS

| | | | |
|---|---|---|---|
| 4,379,462 A | 4/1983 | Borkan et al. ............... 128/786 |
| 4,549,556 A | 10/1985 | Tarjan et al. ................. 128/785 |
| 4,630,611 A * | 12/1986 | King .......................... 600/377 |
| 4,800,898 A | 1/1989 | Hess et al. ................... 128/785 |
| 5,255,691 A | 10/1993 | Otten .......................... 607/117 |
| 5,342,409 A | 8/1994 | Mullett ........................ 607/46 |
| 5,417,719 A | 5/1995 | Hull et al. ..................... 607/46 |
| 5,462,545 A * | 10/1995 | Wang et al. ................... 606/41 |
| 5,571,148 A | 11/1996 | Loeb et al. |
| 5,733,322 A | 3/1998 | Starkebaum ................. 607/117 |
| 5,824,021 A | 10/1998 | Rise ............................ 607/46 |
| 5,902,236 A * | 5/1999 | Iversen ..................... 623/23.65 |
| 6,002,964 A | 12/1999 | Feler et al. ................... 607/46 |
| 6,014,588 A | 1/2000 | Fitz ............................. 607/46 |
| 6,064,905 A * | 5/2000 | Webster et al. ............. 600/424 |
| 6,104,957 A | 8/2000 | Alo et al. ..................... 607/46 |
| 6,128,537 A | 10/2000 | Rise |
| 6,236,892 B1 | 5/2001 | Feler .......................... 607/117 |
| 6,314,325 B1 | 11/2001 | Fitz ............................. 607/46 |
| 6,319,241 B1 | 11/2001 | King et al. ................... 604/502 |
| 2001/0053885 A1 | 12/2001 | Gielen et al. |
| 2002/0062143 A1 | 5/2002 | Baudino et al. |
| 2002/0111661 A1* | 8/2002 | Cross et al. ................. 607/117 |
| 2002/0161403 A1 | 10/2002 | Meadows et al. |
| 2003/0120328 A1* | 6/2003 | Jenkins et al. ............. 607/116 |

FOREIGN PATENT DOCUMENTS

| | | |
|---|---|---|
| EP | 1 048 319 A2 | 3/2000 |
| WO | WO 01/58519 A1 | 1/2001 |
| WO | WO 02/45795 A2 | 12/2001 |

\* cited by examiner

*Primary Examiner*—George Manuel
*Assistant Examiner*—Nicole R. Kramer
(74) *Attorney, Agent, or Firm*—Baker Botts L.L.P.

(57) ABSTRACT

This invention relates to an apparatus and method for making such apparatus for providing controlled and directional stimulation patterns for tissue stimulation. The apparatus may be useful in stimulation nervous tissue in the brain, about the spinal cord, on nerve roots, about peripheral nerves, and in muscles, among others. The apparatus includes a implantable pulse generator connected to a lead. The lead has electrodes placed about a perimeter. In addition, the lead may include electrodes placed longitudinally along the axis of the lead. By applying charge differences between circumferentially distributed electrodes, a smaller stimulation field may be established. In addition, by stimulating between electrodes distributed longitudinally on the same side, a directional flow field may be established. Such leads are especially useful in deep brain stimulation as the region in which a stimulation field is strong enough to produce tissue stimulation is directional and minimized.

11 Claims, 3 Drawing Sheets

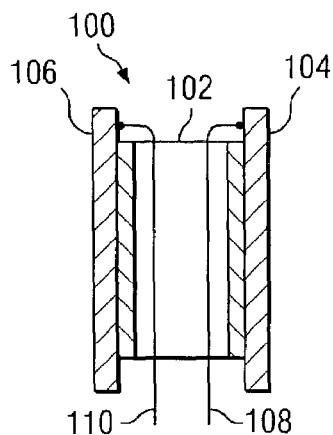
FIG. 6
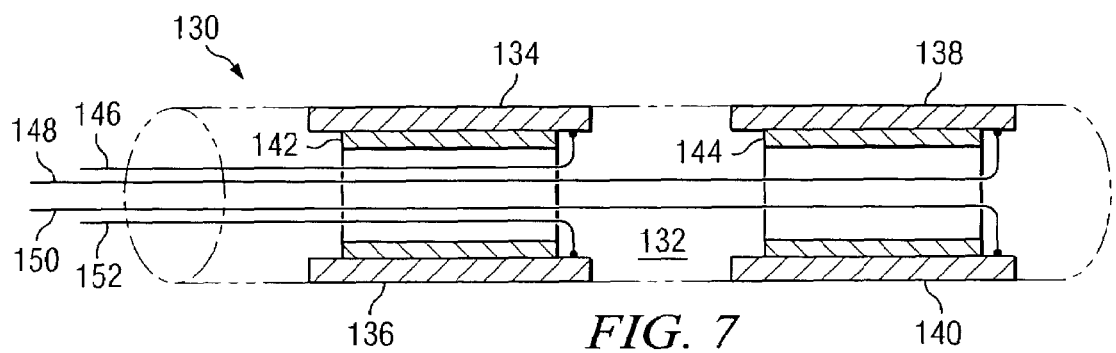
FIG. 7
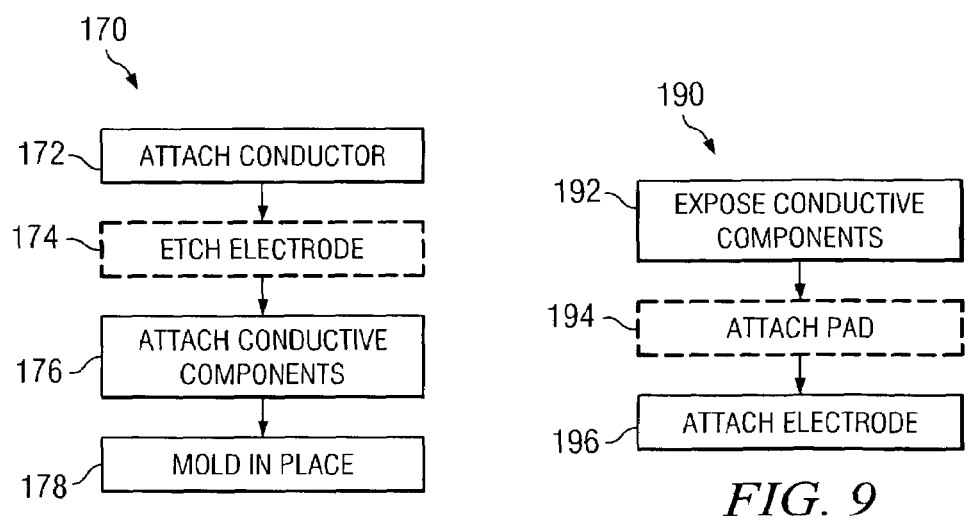
FIG. 8
FIG. 9

APPARATUS FOR DIRECTIONALLY STIMULATING NERVE TISSUE

TECHNICAL FIELD OF THE INVENTION

This invention, in general, relates to electric stimulation of tissue. More specifically, the invention relates to an apparatus and a method for manufacturing such apparatus for directionally stimulating a tissue.

BACKGROUND OF THE INVENTION

Electric stimulation of tissue is used to treat a variety of disorders. Specifically, implantable electric stimulators and leads have been used to treat chronic pain, muscular disorders, hearing problems, symptoms of Parkinson's Disease, bladder control, and sexual dysfunction, among others. Often, a lead terminating in electrodes is situated close to a tissue such as spinal cord, nerve roots, muscles, or brain tissue. An implanted signal generator connected to the lead is then used to generate patterns of electric pulses that stimulate the tissue.

For example, electrodes may be placed in proximity to the spinal cord to treat a variety of ailments. Depending on the placement, electric stimulation will affect various dermatomes about the body. Chronic pain about the leg might be managed by stimulating the spinal cord between the T11 vertebra and the L3 vertebra. Symptoms of Parkinson's Disease and Epilepsy may be treated by placing electrodes about the sub-thalamic region of the brain. In addition, other ailments such as muscular spacticity, incontinence, and sexual dysfunction may be treated by pulse stimulation of an associated tissue.

One typical type of lead is a percutaneous lead. These leads are often designed for easy introduction into an epidural space about the spinal cord using a special needle. As such, these leads are typically cylindrical and terminate at a distal end in one or more cylindrical electrodes distributed longitudinally along the percutaneous lead. A stimulation pulse is typically established by providing opposite charges to one or more electrodes along the lead or between electrodes on adjacent leads. Various pulse amplitudes, pulse widths, frequencies, and intervals, may be used with varying effect on the desired tissue.

However, the stimulation pulses may also affect other tissue in the region. Since the leads are cylindrical, they initiate a charge flow field 360 degrees about the electrode. In many applications where the desired stimulation region is small, the large flow field created by these electrodes stimulates other tissue, having undesired effects.

Controlled tissue stimulation is especially important in deep brain stimulation. The brain is a compact organ in which many differing functions occur in close proximity. Broad stimulation of a small region about the ventrointermediate nucleus of the thalamus could have the positive effect of reducing tremors associated with Parkinson's Disease or cause unwanted side effects such as paresthesia about the head and hands, depression, peresis, dysarthia, loss of balance, or dystonia. Often, patients undergo expensive and painful surgery only to discover that the side effects are to great to continue treatment.

Another area of concern is near the terminal end of the spinal cord. A large number of nerve roots extend from a relatively small region of the spinal cord. Excess stimulation could produce paresthesia in an undesired dermatome or inhibit muscular response in another region.

Another type of lead is paddle-like leads in which electrodes are placed on one side of a flat surface. These electrodes have the disadvantage that they only stimulate in one direction and do not have the option of stimulating in other directions. Misplacement of the electrode can only be corrected by surgery. Often, these electrodes can only establish flow fields longitudinally along the one direction as well. The longitudinal spacing is often large, also causing the stimulation of extra tissue bringing about an undesirable effect.

As such, many leads in electrode configurations suffer from deficiencies caused by the stimulation of extra tissue bringing about undesirable effects. Many other problems and disadvantages of the prior art will become apparent to one skilled in the art after comparing such prior art with the present invention as described herein.

SUMMARY OF THE INVENTION

Aspects of the invention may be found in an apparatus for producing electric stimulation in at least one tissue. The apparatus may include a pulse generator for generating the electric signal and an implantable lead connected to the pulse generator. The implantable lead terminates in a set of electrodes distributed about the perimeter of the implantable lead. Each electrode is individually addressable. The implantable lead may also include several sets of electrodes distributed longitudinally along the axis of the lead. With these electrodes, the apparatus may selectively stimulate on one side of the lead, between the two sides of the same longitudinal point, and in other tortuous paths.

Further aspects of the invention may be found in a lead for stimulating one or more tissues. The lead includes at least one set of electrodes distributed about the perimeter of the lead. Each electrode in the set may be individually addressed. Further, each electrode in the set may be distributed or placed in the same longitudinal position. The cross-sectional shape of the lead may take various forms, including polygons, circles and clovers, among others. Individual electrodes may be distributed one per side or in various allocations. With this distribution, electrodes may be placed 0.5 to 6 millimeters apart and used to stimulate a smaller, more controlled region. Such electrodes may be used in deep brain or subthalamic nucleus stimulation. Alternately, electrodes may be used to directionally stimulate a tissue for applications such as spinal cord stimulation. A lead may also include one or more additional sets of electrodes. Each of these sets may also have electrodes distributed about the perimeter of the implantable lead that are individually addressable. These sets of electrodes may be distributed longitudinally near the distal end of the lead. With this distribution, electrodes may be used to stimulate tissue and select angles about the lead, on a selected side between sets, and in other combinations. Such a lead may be used to stimulate brain tissue such as the subthalamic region, spinal cord and roots, peripheral roots, and muscles, among others.

Another aspect of the invention may be found in a method for stimulating tissue. The method may include the step of applying a voltage difference between at least two electrodes in a set distributed about a perimeter of an implantable lead. Such a stimulation may be applied in the brain, spinal cord or in other regions of the body. The method may also include selecting a configuration of the electrodes and a pulse pattern to apply to the electrodes. Further, the method may include adjusting the configuration of the electrodes to produce a specific result.

An additional aspect of the invention may be found in a method for manufacturing such an implantable lead. The method includes depositing a conductive material on an outer surface of a nonconductive structure. The depositing may be controlled to produce electrodes out of the conductive material or a further etching step may be used to construct the electrodes from the conductive material. The method further includes attaching a unique conductive component to each electrode in a set of electrodes and placing the structure with other similar structures to one end of a mold. The unique components associated with each of the electrodes extend to the opposite end of the mold. The mold is then impregnated with a nonconductive biocompatible material. The nonconductive material or structure may include ceramic material, plastics, or other insulators. The nonconductive biocompatible material may include silicone, polyurethane, polyethylene, polyimide, polyvinylchloride, PTFE, and ETFE, among others. The conductive material may include platinum, titanium, gold, silver, MP35N, stainless steel, platinum-iridium, vanadium, other non-corrosive conductors, amalgams, alloys, and compounds, among others.

As such, an apparatus and a method for making such apparatus has been described. Other aspects, advantages and novel features of the present invention will become apparent from the detailed description of the invention when considered in conjunction with the accompanying drawings.

BRIEF DESCRIPTION OF THE DRAWINGS

For a more complete understanding of the present invention and advantages thereof, reference is now made to the following description taken in conjunction with the accompanying drawings in which like reference numbers indicate like features and wherein:

FIG. 6 is a schematic diagram of an exemplary structure for constructing the lead as seen in FIGS. 2A and 2B;

FIG. 7 is a schematic diagram depicting an exemplary structure for use in the lead as seen in FIGS. 2A and 2B;

FIG. 8 is a block flow diagram depicting an exemplary method for use with the structures as seen in FIGS. 6 and 7; and FIG. 9 is a block flow diagram depicting another exemplary method for producing a lead.

DETAILED DESCRIPTION OF THE INVENTION

Implantable stimulators have been used to treat chronic pain, symptoms of Parkinson's Disease, epilepsy, hearing disorders, depression, and muscle disorders, among others. In each of these applications, the desired treatment area is small and proximate to other tissue for which stimulation would produce undesirable effects. This is especially the case in deep brain stimulation where neural tissue is tightly packed. The nerves in any one region may be responsible for a plethora of functions. For example, excess stimulation in the sub-thalamic region of the brain could lead to paresthesia about the head, loss of balance, depression, peresis, dysarthia, or dystonia. Therefore, it is important to stimulate a small region or a sometimes tortuous path in order to achieve a desired effect. It is also important to avoid stimulating the surround tissue, as that will likely lead to undesired effects.

A similar problem arises when stimulating the spinal cord near its termination. At this point, the spinal cord tapers, extending a large number of neural roots from a small region. Stimulating in a specific direction and between closer electrodes provides more options for selectively stimulating a specific nerve while avoiding the side effects of stimulating other nerve tissue in the region.

Directional stimulation may also limit the power requirement for stimulating a specific tissue. Since the flow field extends through a smaller region, the amount of energy used in creating that flow field would be considerably less than that require to generate a full flow field 360 degrees about a lead. As such, energy savings may be achieved and battery life on implanted devices may be extended.

Figure 1:
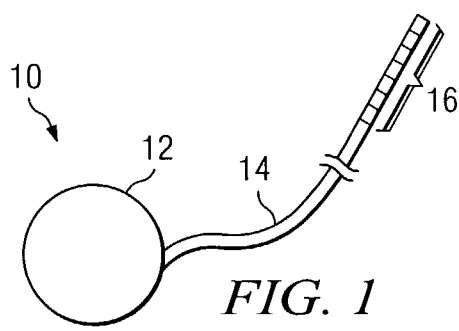
FIG. 1 is a schematic diagram of the apparatus, according to the invention.

FIG. 1 depicts a stimulation system 10 in which the present invention may be utilized. The system 10 includes a pulse generator 12 and a lead 14. The pulse generator 12 may be implantable and may be programmable such as the Renew® or Genesis® systems of Advanced Neuromodulation Systems, Inc. (ANSI). The pulse generator may be comprise RF system and/or battery powered system. The lead 14 may terminate in one or more sets of electrodes 16. The distal end of the lead 14 and the sets of electrodes 16 are placed about the tissue to be treated. The implantable pulse generator then generates pulses or pulse patterns in accordance with a selected configuration to stimulate the tissue. The configuration may include a selection of electrodes and an allocation of charge such as positive, negative, neutral, or some variation for each electrode. In addition, the configuration may include specification of pulse width, pulse amplitudes, pulse intervals, frequencies and other pulse characteristics. Moreover, the pulse characteristics can be varied between multiples of electrodes.

Figure 2B:
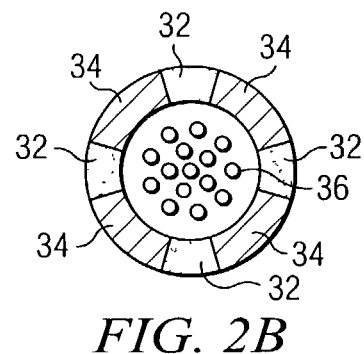
FIGS. 2A and 2B are schematic diagrams of a lead, according to the invention.
Figure 2A:
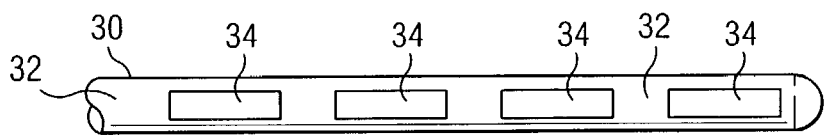

FIGS. 2A and 2B depict an exemplary embodiment of a lead, according to the invention. The lead 30 includes sets of electrodes 34 distributed about the perimeter of the lead 30 and one or more of these sets distributed longitudinally along the lead 30. The electrodes 34 may be surrounded by a nonconductive biocompatible material 32. FIG. 2A depicts the sets of electrodes distributed longitudinally about the distal end of the lead 30. FIG. 2B depicts a cross-sectional view of the lead near one set in which the electrodes 34 can be seen to be distributed about the perimeter of the lead 30, separated by a nonconductive biocompatible material 32.

In the center of the lead are conductive wires 36. Each wire connects to an electrode in a one-to-one relationship enabling individual addressing of each electrode.

The electrodes 34 are typically made of a corrosive-resistant conductive material such as titanium, platinum, vanadium, iridium, silver, gold, surgical steel, stainless steel, MP35N, platinum-iridium, amalgams, alloys, and combinations, among others. The nonconductive biocompatible material 32 may be silicone, polyurethane, polyethylene, polyimide, polyvinylchloride, PTFE, ETFE, ceramics, various biocompatible polymers, or combinations of these, among others. A lead may also comprise, for example, a ceramic support on which the electrodes 34 are deposited, brazed, or electroplated and the nonconductive biocompatible material is supported. Alternately, the electrodes 34 may be deposited on the surface of an insulator.

The individual wires 36 run through the center of the lead. These wires 36 may be insulated conductive wires and/or molded in place with an insulator such as silicon, polymers, ceramics, or combinations of these, among others.

As such, the lead 30 comprises individually addressable electrodes that may produce stimulation patterns about the periphery in addition to stimulation patterns along the axis of the lead 30 or various combinations of these, among others. Controlled stimulation can then be directional by stimulating with adjacent electrodes within a set or electrodes on the same side between sets. This limits the flow field and, more specifically, narrows the region in which the field is strong enough to stimulate. As a result, more focused stimulation areas may be treated.

Figure 3A:
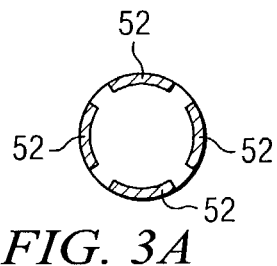
FIGS. 3A, 3B, 3C, 3D and 3E are schematic diagrams depicting an exemplary embodiment of a cross-section of the lead as seen in FIG. 1.
Figure 3B:
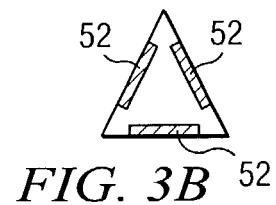
Figure 3C:
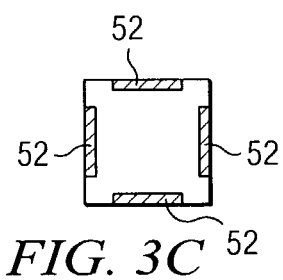

FIGS. 3A, 3B, 3C, 3D and 3E depict various exemplary embodiments of cross-sectional shapes of stimulation leads. Such shaped leads also help to focus the stimulation pattern. FIG. 3A depicts a circular cross-section about which electrodes 52 are distributed. In this case, four electrodes are shown distributed equidistant about a radius. However, fewer or more electrodes may be distributed in this manner. FIG. 3B depicts the triangular cross-section for a lead in which electrodes 52 are present on each side. Similarly, FIG. 3C shows a square cross-section in which the electrodes are distributed one to a side. In both FIGS. 3B and 3C, stimulations may be made between any two adjacent sides actively stimulating about a corner. In all three cases, FIGS. 3A, 3B, and 3C, stimulation flow fields may be induced that travel about the perimeter between adjacent or opposite electrodes. In each case, the flow field is narrower than stimulating across sets of electrodes longitudinally and especially between typical 360 degree stimulators.

Figure 3D:
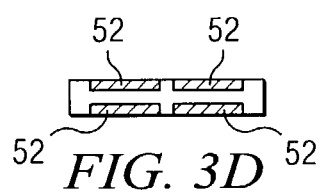

On the other hand, FIG. 3D depicts a lead with more than one electrode on a side. In this example, electrodes 52 are distributed two to a side on two sides of a rectangle. The stimulation flow field may be developed about a side without electrodes by stimulating the two electrodes adjacent to that side. Alternately, a stimulation flow field may be developed on any one side by stimulating the electrodes on the same side.

Figure 3E:
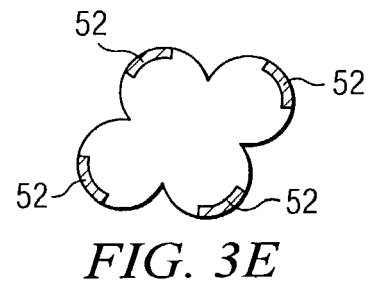

FIG. 3E depicts another exemplary shape, in this case a clover. The electrodes may be placed on the outer surface of the leaves of the clover providing a means of stimulating any one side. However, various shapes including polygons, clovers, circles, ovals, and other irregular shapes may be used.

Sets of these electrodes may be placed longitudinally along a lead. The sets may be arranged such that adjacent sets have parallel or the electrodes may be offset to produce a spiral-like appearance. However, various arrangements of electrodes may be envisaged.

Each of these shapes, among others, may be used to house electrodes or a set of electrodes. Further, the sets of electrodes may be distributed longitudinally along a lead. Moreover, these sets may be distributed along a lead in any peripheral extensions from the lead, providing many possible stimulation flow field configurations.

The leads depicted in FIGS. 2A, 2B, 3A, 3B, 3C, 3D and 3E each have the possibility of producing a flow field about the perimeter of the lead or along one side of the lead. In addition, these electrodes may be used to create a stimulation flow field having a tortuous path about the lead. For example, an electrode on one side of a set of electrodes may be provided with a positive charge while an electrode on an adjacent set on the opposite side may be provided with a negative charge creating a spiraling flow field. It is readily apparent, though, that various flow fields can be envisioned.

Figure 4A:
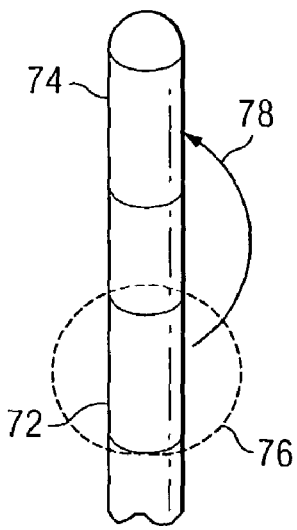
FIGS. 4A, 4B, 4C, and 4D are schematic diagrams of an exemplary embodiment of a lead as seen in FIG. 1.

FIG. 4A depicts a typical prior art lead with electrodes extending around the full circumference of the lead. If electrode 72 is positive and electrode 74 is negative, an equal potential line 76 is established through which current may flow in the direction 78. Such a lead produces the equal potential line 76 and current flow 360 degrees about the lead. If the tissue to be stimulated is on one side of the lead, the additional flow either wastes energy or potentially stimulates tissue having an undesired effect. In deep brain stimulation, the undesired effects could include depression, paresthesia, paresis, dysarthia, and dystonia. In spinal cord stimulation, the undesired effects could include paresthesia in an undesired location, dystonia, or loss of muscle control.

Figure 4B:
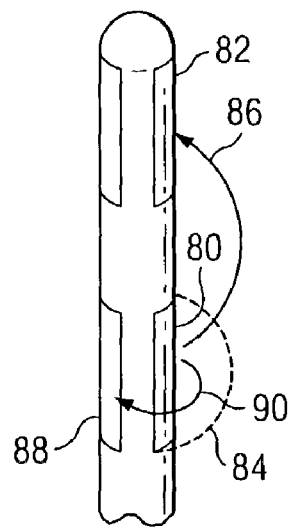

FIG. 4B depicts a lead having electrodes distributed radially about the lead as well as longitudinally. Electrodes may be placed 0.5–6 mm apart longitudinally for spinal cord stimulation leads and for deep brain and sub-thalamic region leads. However, various separations may be used for various applications. If electrode 80 is positive and electrode 82 is negative, current may flow from electrode 80 to 82. In this case, the equal potential line 84 resides to one side of the lead, stimulating a narrower region. In another case, if an electrode 80 is positive and an electrode 88 is negative, current will flow in a path 90 between the two electrodes 80 and 88. In this way, a more focused region can be stimulated about a select volume of the lead.

Figure 4C:
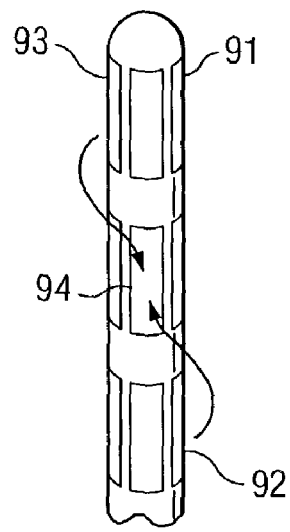

More complex patterns may also be accomplished. FIG. 4C depicts a spiraling pattern created by placing opposite charge on electrodes in adjacent sets. A current flows from the positive electrodes 92 and 93 to the negative electrode 94. Such a pattern may be useful in following the tortuous path of a specific nerve. Alternately, the pattern may be used for a lead spiraled about a nerve root to keep the stimulation field directed into the nerve root.

Figure 4D:
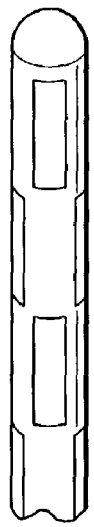

FIG. 4D depicts an exemplary embodiment of a lead in which adjacent sets of electrodes are staggered. Electrodes may also be placed in patterns that concentrate the electrodes in regions about the lead. Further patterns may be created if the stimulator or generator has a charged outer surface. In this manner, stimulators can act as electrodes.

Figure 5:
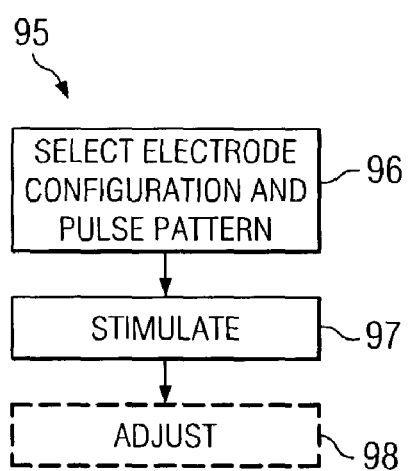
FIG. 5 is a block flow diagram of an exemplary method produced by the system as seen in FIG. 1.

FIG. 5 depicts an exemplary method for use with the system. In the method 95, an electrode configuration and pulse pattern is established in an implantable pulse generator as seen in block 96. The electrode configuration and pulse pattern establishes the charge allocation to the various electrodes and a pattern of pulse widths, pulse amplitudes, frequencies, intervals between pulses and other pulse characteristics useful in stimulating the desired tissue. The system then provides pulses in accordance with the electrode configuration and pulse pattern to stimulate the tissue as seen in block 97. In response, the electrodes develop the desired flow field about the tissue. This flow field may, for example, be established between electrodes on the perimeter of the lead. Alternately, it may be established between the electrodes longitudinally displaced along the lead or in various combinations. In this manner, the region in which the stimulation flow field provides a strong enough charge flow to stimulate the tissue is limited to smaller, less than 360 degree regions within the tissue.

The method may be further applied to the establishment of a desired stimulation effect by adjusting the electrode configuration and pulse patterns to achieve the desired effect as seen in a block 98. For example, a surgeon may select an electrode configuration and pulse pattern, stimulate the tissue and evaluate the results, adjusting the chosen electrodes to fine tune or produce a desired effect.

The above method may be applied in the treatment of various ailments. In the treatment of Parkinson's Disease, electrodes may be placed about the vetrointermediatal nucleus of the thalamus. A surgeon may select an electrode configuration and test it for effectiveness and undesired side effects. The configuration may be adjusted to improve effectiveness and relieve side-effects. Similarly, the system may be used to treat chronic pain or muscular disorders through the stimulation of the spinal cord.

The electrodes seen in FIGS. 2A, 2B, 3A, 3B, 3C, 3D, 3E, 4B may be produced or manufactured through various methods. These methods include placing electrodes in a mold; sputtering, electroplating, and chemically depositing conductive material on a structured surface; and sintering a metal or composite material to form a three-dimensional structure; among others. The electrodes may further be etched or polished to produce a clean smooth surface. Nonconductive biocompatible material may also be placed between electrodes to provide a smooth uninterrupted surface.

FIG. 6 depicts a cross-section of an exemplary structure for use in the manufacture of the electrodes as seen in FIGS. 2A, 2B, 3A, 3B, 3C, 3D, 3E, 4B. This exemplary structure includes a nonconductive core 102 upon which electrodes 104 and 106 are attached. The attaching may include electroplating, sputtering, brazing, chemical deposition, plasma deposition, laser sintering, and layering, among others. Etching and polishing may further be used to established individual electrodes or provide a smooth surface.

Individual wires 108 or 110 can be coupled to the electrodes 104 or 106, respectively. Techniques such as welding, soldering, and joining may be used to couple wires to electrodes. In this case, the wires 108 and 110 are within or through the structure 102. These wires may be pre-insulated or held separate to prevent current flow between the wires 108 or 110.

Alternately, various conductive structures may be used in place of wires. For example, these conductive structures may be solid wires, drawn-filled-tubes, drawn-brazed-strands, and stranded cables, among others. In addition, the wires and/or structures may be integrated with the structure 102.

The structure 102 may be made from a nonconductive material such as ceramics, polymers, silicone, polyurethane, composites, or combinations, among others. The electrodes 104 and 106 may be made from various non-corrosive conductors including platinum, platinum-iridium, titanium, stainless steel, gold, silver, MP35N, amalgams, alloys, and composites, among others.

Several of these structures can then be distributed longitudinally within a mold to provide various sets of electrodes. FIG. 7 depicts two of such structures distributed along a lead. The structures 142 and 144 are surrounded by a nonconductive biocompatible material 132 such that the electrodes 134, 136, 138 and 140 fit flush with the surface. Wires 146, 148, 150 and 152 are located within or through structures 144 and 142 and terminate at an opposite end of the lead 130 in connectors operably designed to connect to an implantable pulse generator. The biocompatible nonconducting or insulative material 132 may be silicone, polyurethane, polyethylene, polyimide, polyvinylchloride, PTFE, ETFE, biocompatible polymers, ceramics, or various combinations of these, among others. Successive sets of electrodes may also be angularly offset to produce additional potential stimulation patterns.

A method for making such a lead may be seen in FIG. 8. Conductive material is deposited on a structure using various techniques as seen in a block 172. The depositing may include electroplating, sputtering, chemical deposition, plasma deposition, laser sintering, and layering, among others. Using these methods, the deposition may be specific, creating shaped electrodes or may require additional work to separate and prepare the electrodes. For example, the system may require additional etching to separate the conductive material into electrodes as seen in a block 174. In addition, etching may be used to prepare the surface of the electrodes.

Once these structures are prepared with electrodes, individual wires are attached to each electrode as seen in 176. This attaching or coupling may include soldering, sintering, welding, and other techniques.

Subsequently, several structures are placed in a mold about the distal end of what is to become a lead. The wires run through the middle or center of this mold or form. The mold or form is then impregnated with a insulative or nonconductive biocompatible material, forming the lead. This nonconductive biocompatible material may be silicone, polyurethane, or some other biocompatible polymer, among others. The advantage to using silicone or other biocompatible polymers is their flexibility, useful in the placement of the leads. However, various other materials and methods of manufacturing leads with electrodes distributed about the perimeter of the leads may be envisaged.

FIG. 9 depicts an alternate method for making a lead. Conductors are exposed through an outer surface of an insulating structure as seen in a block 192. This exposure may be accomplished by laser etching, and physical means, among others. The exposed conductor may then be attached to a pad as seen in block 194. The pad may be attached or formed through sintering, welding, soldering, adhering, electroplating, brazing, deposition, and combinations, among others. An electrode may then be attached or formed to the pad as seen in block 196. This may be accomplished through sintering, welding, soldering, adhering, electroplating, brazing, deposition, and combinations, among others.

A similar method may be found in U.S. patent application Ser. No. 09/822,728, filed Mar. 30, 2001 and entitled "Medical Lead and Method for Electrode Attachment", which is included by reference here in its entirety.

As such, an apparatus and method for making such apparatus is described. In view of the above detailed description of the present invention and associated drawings, other modifications and variations will now become apparent to those skilled in the art. It should also be apparent that such other modifications and variations may be effected without departing from the spirit and scope of the present invention as set forth in the claims which follow.

We claim:

1. A lead for stimulating one or more tissues, the lead comprising:
    a set of electrodes distributed about a perimeter of the lead, each electrode in the set of electrodes being individually addressable;
    a biocompatible non-conductive material interspersed among the set of electrodes; and
    a set of conductive components, each component in the set of conductive components uniquely associated with an electrode in the set of electrodes;
    the cross-section of the lead being in the shape of a clover, the set of electrodes being distributed one per leaf of the clover.

2. The lead of claim 1, wherein adjacent electrodes distributed about the perimeter are situated less than 1 mm apart.

3. The lead of claim 1, wherein the set of electrodes is adapted to be placed in proximity to the ventrointermediate nucleus of the thalamus.

4. The lead of claim 1, wherein the set of electrodes is adapted to be placed in proximity to the subthalamic region.

5. The lead of claim 1, wherein the set of electrodes is adapted to be placed in proximity to the spinal cord.

6. The lead of claim 1, wherein the set of electrodes is adapted to be placed in proximity to a nerve root.

7. The lead of claim 1, wherein the lead is adapted to stimulate the one or more tissues in a stimulation pattern established by providing a positive charge to at least one electrode in the set of electrodes and a negative charge to at least one other electrode in the set of electrodes.

8. The lead of claim 1, wherein the lead is adapted to stimulate the one or more tissues in a stimulation pattern established by providing a charge to at least one electrode in the set of electrodes and an opposite charge to an external surface of a pulse generator.

9. The lead of claim 1, further comprising:
one or more additional sets of electrodes, each electrode in the one or more additional sets of electrodes being individually addressable and distributed about the perimeter of the lead, the one or more additional sets of electrodes being distributed longitudinally along the lead.

10. The lead of claim 9, wherein adjacent sets of electrodes are located between 0.5 and 6 mm apart longitudinally.

11. The lead of claim 9, wherein the lead is adapted to stimulate the one or more tissues in a stimulation pattern established by providing a positive charge to at least one electrode in a set of electrodes and a negative charge to at least one other electrode in an adjacent set of electrodes, the at least one other electrode being on the same side of the lead as the at least one electrode.

* * * * *